(12) United States Patent
Velaga

(10) Patent No.: US 12,354,319 B2
(45) Date of Patent: Jul. 8, 2025

(54) REAL-TIME DOCUMENTATION VERIFICATION USING ARTIFICIAL INTELLIGENCE AND MACHINE LEARNING

(71) Applicant: ORBIT HEALTHCARE, INC., East Brunswick, NJ (US)

(72) Inventor: Krishna Velaga, East Brunswick, NJ (US)

(73) Assignee: ORBIT HEALTHCARE, INC., East Brunswick, NJ (US)

( * ) Notice: Subject to any disclaimer, the term of this patent is extended or adjusted under 35 U.S.C. 154(b) by 599 days.

(21) Appl. No.: 17/188,195

(22) Filed: Mar. 1, 2021

(65) Prior Publication Data

US 2022/0277167 A1 Sep. 1, 2022

(51) Int. Cl.
*G06V 10/40* (2022.01)
*G06F 18/21* (2023.01)
(Continued)

(52) U.S. Cl.
CPC ............ *G06V 10/40* (2022.01); *G06F 18/217* (2023.01); *G06N 20/00* (2019.01); *G06Q 10/10* (2013.01);
(Continued)

(58) Field of Classification Search
CPC ......... G16H 40/20; G06Q 10/10; G06N 20/00
See application file for complete search history.

(56) References Cited

U.S. PATENT DOCUMENTS 5,832,447 A 11/1998 Reiker et al.
8,442,844 B1 5/2013 Trandal et al.
(Continued)

FOREIGN PATENT DOCUMENTS

JP 2007048146 A 2/2007
RU 2607270 C2 1/2017

OTHER PUBLICATIONS

Hauser, Susan, Tehseen Sabir, and George Thoma. "OCR correction using historical relationships from verified text in biomedical citations." Proc. 2003 Symp. on Document Image Understanding Technology. 2003. (Year: 2003).*

(Continued)

*Primary Examiner* — Matthew C Bella
*Assistant Examiner* — Johnny B Duong
(74) *Attorney, Agent, or Firm* — Jason A. Smith; Shumaker, Loop & Kendrick, LLP

(57) ABSTRACT

A method to verify documentation, such as healthcare documentation, in real-time is described. An image of a first document and demographic information is received from a patient. Optical character recognition (OCR) or QR code, barcode, or machine readable zone (MRZ) reading is performed on the image of the first document and a patient identifier is extracted from the first document. The patient identifier is compared to content in a database to identify a second document related to the first document that shares the patient identifier with the first document. The first document and the second document are verified as being associated with the patient based on the comparison and predefined business rules. OCR errors are identified in the first document and corrected using content from the second document. The method occurs prior to and allows the patient to pay for a healthcare appointment prior to attending the appointment.

18 Claims, 11 Drawing Sheets

(51) Int. Cl.
  *G06N 20/00* (2019.01)
  *G06Q 10/10* (2023.01)
  *G06Q 20/08* (2012.01)
  *G06V 30/10* (2022.01)
  *G06V 30/146* (2022.01)
  *G06V 30/418* (2022.01)
  *G16H 10/20* (2018.01)
  *G16H 10/60* (2018.01)
  *G16H 40/20* (2018.01)
  *G16H 50/70* (2018.01)

(52) U.S. Cl.
  CPC ......... *G06Q 20/085* (2013.01); *G06V 30/418* (2022.01); *G16H 10/20* (2018.01); *G16H 10/60* (2018.01); *G16H 40/20* (2018.01); *G16H 50/70* (2018.01); *G06V 30/10* (2022.01); *G06V 30/147* (2022.01)

(56) References Cited

U.S. PATENT DOCUMENTS

| | | | |
|---|---|---|---|
| 9,396,388 B2* | 7/2016 | Amtrup | G06V 30/40 |
| 2002/0082863 A1 | 6/2002 | Muszynski | |
| 2003/0191665 A1* | 10/2003 | Fitzgerald | G16H 50/20 |
| | | | 705/2 |
| 2004/0249665 A1 | 12/2004 | David | |
| 2005/0192838 A1 | 9/2005 | Jones et al. | |
| 2006/0047539 A1* | 3/2006 | Huang | G06Q 10/10 |
| | | | 705/2 |
| 2012/0316893 A1* | 12/2012 | Egawa | G06Q 40/08 |
| | | | 705/2 |
| 2013/0204645 A1 | 8/2013 | Lehman et al. | |
| 2016/0275252 A1* | 9/2016 | Anderson | G06Q 10/103 |
| 2020/0126227 A1* | 4/2020 | Adiri | G06V 10/82 |
| 2021/0124919 A1* | 4/2021 | Balakrishnan | B42D 25/309 |
| 2021/0174109 A1* | 6/2021 | Beller | G06V 30/416 |
| 2021/0209694 A1 | 7/2021 | Tabbaa et al. | |
| 2022/0148053 A1* | 5/2022 | Lockhart | G06Q 20/102 |
| 2022/0159129 A1* | 5/2022 | Abe | H04N 1/00082 |
| 2022/0164573 A1* | 5/2022 | Chikyu | G06V 30/418 |

OTHER PUBLICATIONS

Non-Final Office Action (NFOA) issued for U.S. Appl. No. 18/097,790 mailed Jun. 13, 2023 (31 pages).

Notice of Allowance (NOA) issued for U.S. Appl. No. 18/097,790 dated Aug. 21, 2023 (13 pages).

* cited by examiner

REAL-TIME DOCUMENTATION VERIFICATION USING ARTIFICIAL INTELLIGENCE AND MACHINE LEARNING

FIELD OF THE EMBODIMENTS

The field of the invention and its embodiments relate to a documentation verification system and method. In particular, the field of the invention and its embodiments relate to a real-time healthcare insurance verification system and method that utilizes artificial intelligent and/or machine learning to capture data from a front and a back of an insurance card.

BACKGROUND OF THE EMBODIMENTS

When a patient visits a healthcare providers office for an appointment, the patient shows proof of healthcare insurance (if any) and pays a co-payment for the appointment (if any). Such physical and contact-based exchange of documentation and payment increases the exposure and spread of COVID-19, as well as other diseases and/or illnesses. The health insurance is then processed and applied to the total cost of the appointment. After the appointment, the patient receives, in the mail or electronically, an invoice for the appointment, with the health insurance being applied to the overall cost of the appointment. As such, prior to the appointment, the patient is unaware of the true cost of the appointment, resulting in approximately 70% of consumers indicating that healthcare makes payments more difficult than any other industry.

Moreover, during the processing of the healthcare insurance, manual errors occur, resulting in unexpected, inaccurate, and increased costs associated with the appointment. Every year, $190 billion is spent unnecessarily in administration of healthcare payments. Further, 25% of wasted spending in healthcare is directed to time and money spent on collecting, posting, and reconciling payments. Additionally, each payment may be processed at a different time in the payment cycle, resulting in a lack of consistency and high error rates.

Further, during this processing, 10% of insurance claims are denied and 35% of these denied claims are reworked and resubmitted. The work required to resubmit claims is up to eighteen times more than a claim correctly filed initially. Common mistakes that cause claim denial include: incorrect patient identification information, services rendered at the appointment that are not covered by the healthcare insurance, the provider who rendered the appointment is an out-of-network provider for the healthcare insurance, and prior authorization was required by the third-party insurer prior to the appointment. These mistakes can also occur when manual data transfer is required between differing system. Eliminating the reworking of 100 claims a month could save an average healthcare practice $37,000 a year and, for a hospital, this number could be as great as $149,000 a year.

Thus, what is needed is a system that involves the contactless transfer of documentation and payment and provides an upfront cost estimation to the patient before the patient goes to the appointment. Such system may include the pre-registration of any necessary identification data (e.g., a driver's license, a health insurance card, demographic data, etc.), confirmation that the health insurance coverage is valid on the date of service (e.g., the date of the healthcare appointment), confirmation of any patient payment responsibility, and confirmation or authorization of any referral requirements.

REVIEW OF RELATED TECHNOLOGY

U.S. Published Patent Application No. 2014/0254887 A1 describes a computer program product that includes a computer readable storage medium having embodied thereon program code readable/executable by at least one processor. The program code is configured to cause the at least one processor to: receive an image of a document. The document may be: a gift card, an invoice, a bill, a receipt, a sales order, an insurance claim, a medical insurance document, or a benefits document, among others. Then, the program code is further configured to cause the at least one processor to: perform optical character recognition (OCR) on the image, extract an address of a sender of the document from the image based on the OCR, compare the extracted address with content in a first database, identify complementary textual information in a second database based on the address, and (1) extract additional content from the image of the document, (2) correct one or more OCR errors in the document using the complementary textual information, and/or (3) normalize data from the document prior to determining a validity of the document using at least one of the complementary textual information and one or more predefined business rules.

WO 2013/061158 A2 describes a system and method for gathering patient information and completing patient information forms across multiple practice groups. An aggregator utilizes the patient information forms provided by different groups to create marked-up forms and a library of questions. In one example, the forms are collected from various practice groups, stored and processed as an image or converted (e.g., via OCR) from an image into searchable data or text and then individually marked-up with an application tool, with or without assistance of a human operator. The aggregator can then present ordered sets of questions from the library to a patient to obtain patient information for responding to the requests in one or more forms.

CA3002447A1 describes a system for a user with a mobile device to scan a patient health record identifier. The mobile device is coupled via a network to a health record database. The system comprises a patient health application installed on the mobile device. The system is configured to: select a font, produce a region of interest detection window on the mobile device, capture an image of a patient health record identifier, perform one or more pre-processing operations on the captured image to produce a pre-processed image, perform one or more OCR operations on the pre-processed image using the selected font to extract the patient health record identifier, perform one or more post-processing operations on the extracted health record identifier to verify the extracted patient health record identifier, and retrieve patient information from the health record database based on the verified and extracted patient health record identifier. The patient health record identifier may be a health card number such as a health insurance policy number and/or a medical institution record identifier supplied by a medical institution such as a clinic, hospital, or testing facility.

WO 2007/081147 A1 describes a method that includes: a) determining a character feature for each field of a name card (e.g., any documentation that includes a name of the user); b) extracting a character area from a name card image captured by using the camera when in a name card recognition mode; c) extracting a candidate area for each field, which is estimated to contain information on a field to be extracted from the name card image, by using the character feature for each field; d) extracting character information of each field candidate having a top priority from the candidate area for each field; and e) integrating each extracted character information. An example of the character recognition system includes: an OCR system that can recognize both a printed character and a handwritten character.

CN108961077A describes an OCR-based medical insurance reimbursement system. The system includes: an identity acquisition unit, an identity check unit, a settlement unit, and a detail query unit. The identity acquisition unit acquires doctor identity information and resident identity information through an OCR recognition technology. The identity check unit is used for checking the doctor identity information and the resident identity information. The settlement unit is used for clearing the reimbursement expenses of residents and automatically deducting the reimbursement expenses from the medical insurance accounts of the residents. The detail query unit queries the settlement details of the settlement unit and returns the settlement details. Further, the identity acquisition unit is connected with the identity check unit and the identity check unit is connected with the settlement unit. The settlement unit is connected with the detail query unit.

U.S. Pat. No. 8,345,981 B2 describes a method. The method includes numerous process steps, such as: performing OCR on a scanned image of a first document, extracting an identifier from the first document, identifying a complementary document associated with the first document using the identifier, generating a list of hypotheses mapping the first document to the complementary document using (a) textual information from the first document, (b) textual information from the complementary document, and (c) predefined business rules, correcting OCR errors in the first document using at least one of the textual information from the complementary document and the predefined business rules, determining a validity of the first document based on the hypotheses, and outputting an indication of the determined validity.

Various documentation verification systems exist. However, their means of operation are substantially different from the present disclosure, as the other inventions fail to solve all the problems taught by the present disclosure.

SUMMARY OF THE EMBODIMENTS

The present invention and its embodiments relate to a documentation verification system and method. In particular, the present invention and its embodiments relate to a real-time healthcare insurance verification system and method that utilizes artificial intelligent and/or machine learning.

A first embodiment of the present invention describes a system configured to verify documentation in real-time. The system includes a computing device and a verification system. An application (such as a provider application or engine) is executable on the computing device. The application is configured to: receive an image of a first document from a patient and transfer the image of the first document to the verification system.

The verification system is configured to: receive the image of the first document from the application and perform optical character recognition (OCR) or QR code, barcode, or machine readable zone (MRZ) reading on the image of the first document. Performing the OCR on the image of the first document includes: pre-processing the first document. The pre-processing may occur via one or more machine learning algorithms and/or artificial intelligence algorithms, among others, and may include: de-skewing the first document, cropping the image of the first document, reducing noise for the first document, de-speckling the first document, binarisating the first document, removing lines from the first document, analyzing a layout of the first document, detecting lines in the first document, detecting words in the first document, recognizing script in the first document, and/or isolating characters in the first document, among other processes not explicitly listed herein.

Performing the OCR on the image of the first document also includes utilizing one or more text recognition algorithms, such as: a matrix matching algorithm and/or a feature extraction algorithm, among others. The performance of the OCR on the image of the first document also includes post-processing the first document.

The verification system is further configured to: extract a patient identifier and information from the first document. The patient identifier can be any combination of letters, words, numbers (e.g., the last four numbers of the patients' social security number), etc. that identify a particular patient. The verification system then compares the patient identifier to content in a database to identify the second document related to the first document and sharing the patient identifier with the first document. The database may be a healthcare provider database or a third party insurer database, among others not explicitly listed herein. The first document and the second document may be an invoice, a receipt, a bill, a sales order document, an insurance claim document, a driver's license, a passport, an explanation of benefits document, or a medical insurance document, among other documents not explicitly listed herein.

The verification system is further configured to: verify the first document and the second document as being associated with the patient based on the comparison and predefined business rules. Moreover, the verification system is configured to: utilize a weighted average mechanism to assign a confidence score to the match between the first and the second document.

Such post-processing of the first document includes identifying one or more OCR errors in the first document and correcting the one or more OCR errors in the first document using the content from the second document.

A second embodiment of the present invention describes a method executed by a system to verify documentation in real-time. The method includes numerous process steps, such as: receiving an image of a first document from a patient via a website associated with the system, receiving information from the patient via the web site associated with the system, performing the OCR on the image of the first document, and extracting a patient identifier and information from the first document. The method also includes: comparing the patient identifier to content in a database to identify a second document related to the first document that shares the patient identifier with the first document.

In some examples, the method further includes: verifying the first document and the second document as being associated with the patient based on the comparison and predefined business rules. The method may additionally include: identifying one or more OCR errors in the first document and correcting the one or more OCR errors in the first document using the content from the second document.

In some examples, the first document comprises a medical insurance document. In this example, the method further comprises transmitting an inquiry to the database to confirm a status of health insurance benefits associated with the medical insurance document prior to the patient attending a healthcare appointment. The method may additionally include identifying the status of the health insurance benefits as being current and applying the health insurance benefits associated with the medical insurance document to the cost of the appointment to reduce the cost of the appointment in real-time. The method may further include transmitting the modified payment to the website for display to the patient, prompting the patient to pay the modified payment via the website, receiving the payment, and processing the payment for the appointment.

In other examples, the method further includes: failing to verify the first document and the second document as being associated with the patient based on the comparison and the predefined business rules. In this scenario, the method may further include: generating an alert and transmitting the alert to a human for reconciliation.

A third embodiment of the present invention describes a computer system. The computer system includes one or more processors, one or more memories, and one or more computer-readable hardware storage devices. The one or more computer-readable hardware storage devices contain program code executable by the one or more processors via the one or more memories to implement a method to verify documentation in real-time. The method includes numerous process steps, such as: receiving an image of a first document from a patient, performing OCR or QR code, barcode, or machine readable zone (MRZ) reading on the image of the first document, and extracting a patient identifier from the first document.

The method may further include: comparing the patient identifier to content in a database to identify a second document related to the first document and sharing the patient identifier with the first document. The method additionally includes: verifying the first document and the second document as being associated with the patient based on the comparison and the predefined business rules. The method further includes: identifying one or more OCR errors in the first document and correcting the one or more OCR errors in the first document using the content from the second document. The method also includes: utilizing a weighted average mechanism to assign a confidence score to the match between the first and the second document.

In some examples, the first document comprises a medical insurance document and the method further comprises transmitting an inquiry to the database to confirm a status of health insurance benefits associated with the medical insurance document prior to the patient attending an appointment. In this instance, the method further includes: identifying the status of the health insurance benefits as being current and applying the health insurance benefits associated with the medical insurance document to the total cost of the appointment to reduce the total cost of the appointment in real-time. The method also includes: displaying the modified payment to the patient, prompting the patient to pay the modified payment, receiving the payment, and processing the payment for the appointment.

In other examples, in response to failing to verify the first document and the second document as being associated with the patient based on the comparison and predefined business rules, the method further comprises generating an alert and transmitting the alert to a human for reconciliation. The alert may be an audio alert, a textual alert, and/or a graphical alert, among others.

In general, the present invention succeeds in conferring the following benefits and objectives.

It is an objective of the present invention to provide a method and a system to verify documentation in real-time.

It is an objective of the present invention to provide a method and a system to verify healthcare documentation (such as healthcare insurance documentation) in real-time.

It is an objective of the present invention to provide a method and a system to verify healthcare documentation (such as healthcare insurance documentation) in real-time using artificial intelligence (AI), machine learning (ML), and/or optical character recognition (OCR).

It is an objective of the present invention to provide a system that allows a patient to easily and contactlessly "check-in" for a healthcare appointment from anywhere.

It is an objective of the present invention to provide a system that allows a patient to easily and contactlessly "check-in" for a healthcare appointment from anywhere to reduce the risk of exposure to and spread of COVID-19 and similar diseases/illnesses.

It is an objective of the present invention to provide a method and a system that allows a patient to understand the financial cost and responsibility of a healthcare appointment prior to receiving the service of the healthcare appointment.

It is an objective of the present invention to provide a system that easily saves and stores patient information such that the patient need not carry his/her health insurance card and other identifying documentation to the appointment.

It is an objective of the present invention to provide a system that reduces administrative workload for greater productivity and cost savings.

It is an objective of the present invention to provide a system that allows for accurate data capture and digital insurance verification for faster claims processing.

It is an objective of the present invention to provide a system that reduces the number of administrative errors and turnover.

It is an objective of the present invention to provide a system that reduces mistakes and reworking of healthcare claims from misreading healthcare insurance cards.

It is an objective of the present invention to provide a system for automated insurance eligibility verification.

It is an objective of the present invention to provide a system that allows for quick confirmation that the health insurance coverage is valid on the date of service, confirmation of any patient payment responsibility, and confirmation or authorization of any referral requirements.

DESCRIPTION OF THE PREFERRED EMBODIMENTS

Figure 1A:
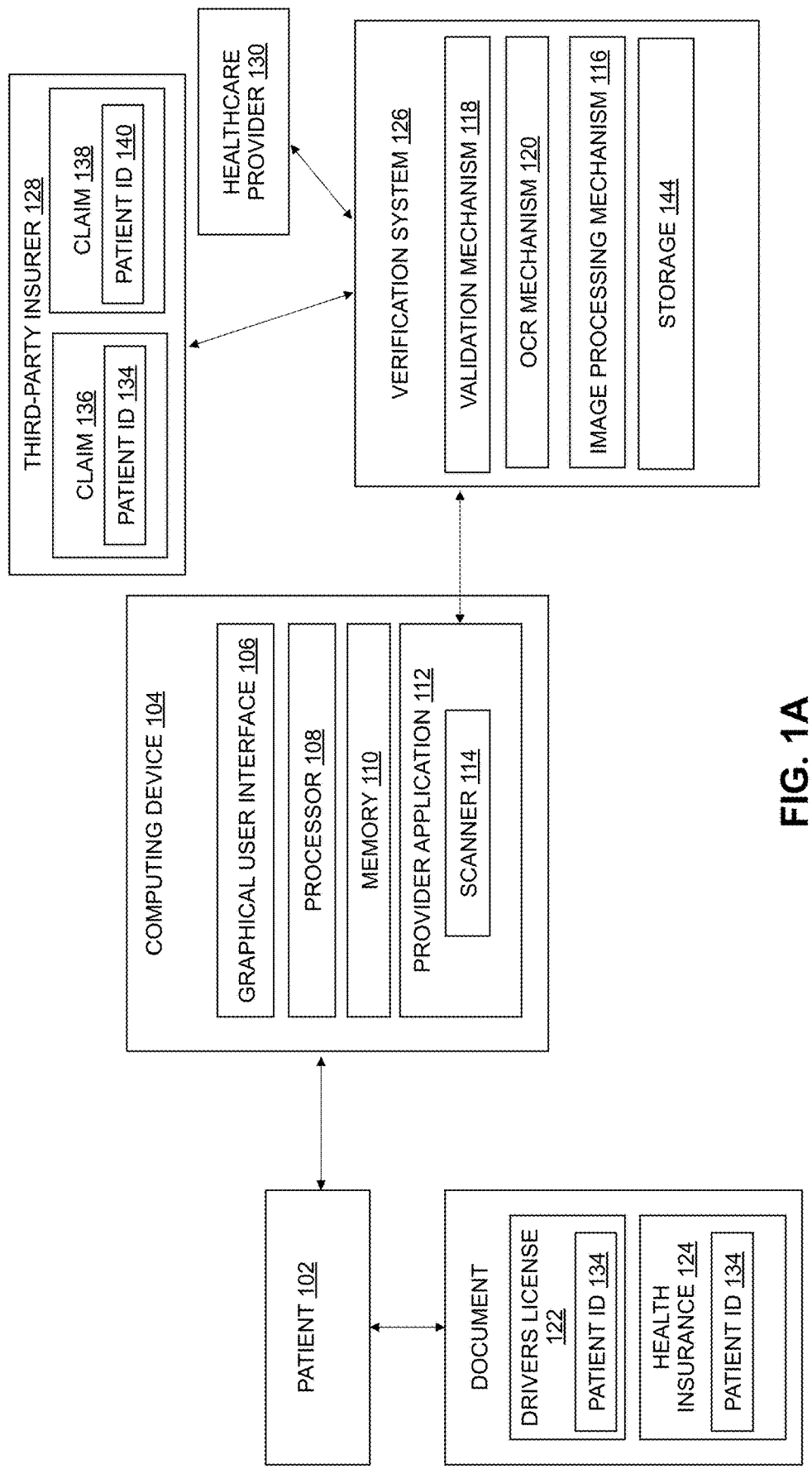
FIG. 1A and FIG. 1B depict block diagrams of a system to verify documentation in real-time, according to at least some embodiments disclosed herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

When a patient visits a healthcare providers office for an appointment, the patient physically hands proof of healthcare insurance (if any) and pays a co-payment for the appointment (if any). Such physical exchange of documentation and payment increases the potential exposure to and spread of COVID-19, as well as other diseases and/or illnesses. Next, the health insurance is processed and applied to the total cost of the appointment. After the appointment, the patient receives, in the mail or electronically, an invoice for the appointment, with the health insurance being applied to the overall cost of the appointment. Thus, the patient is unaware of what the true cost of the healthcare appointment is prior to the appointment and may be surprised by the required payment received subsequent the appointment.

The system and method described herein in FIG. 1A-FIG. 10 involves the contactless transfer of documentation and payment, which provides an upfront cost estimation to the patient before the patient attends the appointment. Such system and method of FIG. 1A-FIG. 10 may include the pre-registration of any necessary identification data (e.g., a driver's license, a health insurance card, demographic data, etc.), confirmation that the health insurance coverage is valid on the date of service (e.g., the date of the healthcare appointment), confirmation of any patient payment responsibility, and confirmation or authorization of any referral requirements prior to attending the healthcare appointment.

Figure 1B:
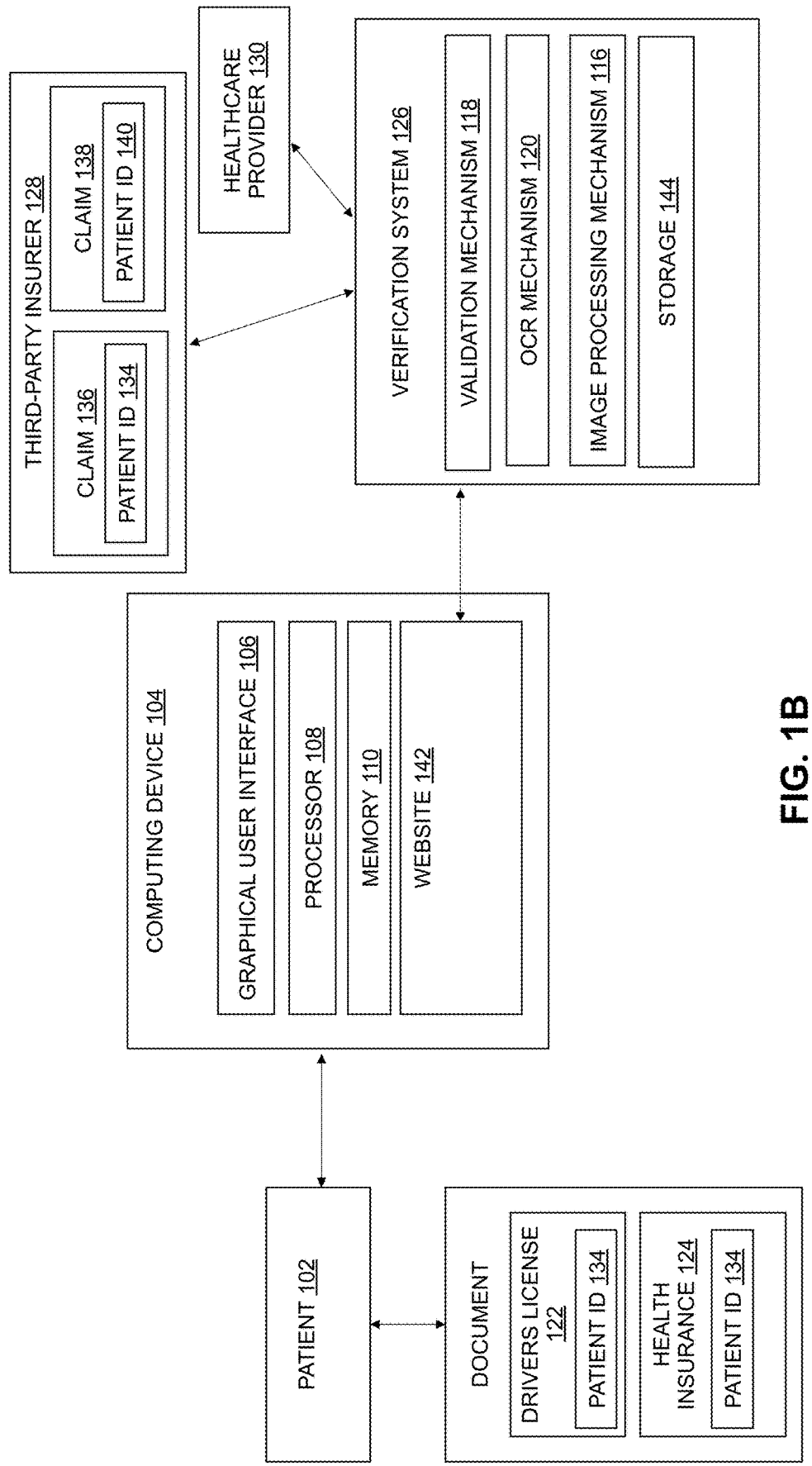

FIG. 1A and FIG. 1B depict block diagrams of a system to verify documentation in real-time, according to at least some embodiments disclosed herein.

The system of FIG. 1A and FIG. 1B includes a computing device 104, a verification system 126, and a repository/database. The computing device 104 may be a computer, a laptop computer, a smartphone, and/or a tablet, among other examples not explicitly listed herein. The computing device 104 includes, at least, a processor 108, a memory 110, a graphical user interface (GUI) 106, and a provider application 112 (of FIG. 1A). In other implementations, the provider application 112 may be an engine, a software program, a service, or a software platform configured to be executable on the computing device 104. The database may include a third-party insurer database 128 and/or a healthcare provider database 130, among others not explicitly listed herein.

The verification system 126 may include numerous applications, components, and/or engines that are configured to receive and validate or verify information from documentation in real-time. For example, as shown in FIG. 1A and FIG. 1B, the verification system 126 includes: a validation mechanism 118, an optical character recognition (OCR) mechanism 120, storage 144, and/or an image processing mechanism 116, among others.

In an example, the provider application 112 may prompt the patient 102 to input information to the provider application 112 using the GUI 106, such as: a name, an address, a telephone number, appointment information, healthcare coverage information, and other demographic information, etc. In other examples, the verification system 126 may transmit a link, an SMS message, or an email message to the computing device 104. The patient 104 may then use the GUI 106 of the computing device 104 to open the link, the SMS message, or the email message and provide the requested information. In preferred examples, this information may be related to a healthcare provider appointment.

The provider application 112 is then configured to: receive an image of a first document (e.g., a driver's license 122, a health insurance document 124, an invoice, a receipt, a bill, a sales order document, an insurance claim document, a passport, or an explanation of benefits document, among other documents not explicitly listed herein) from the patient 102. The image is received using HIPAA complaint methods. In some examples, the provider application 112 is configured to receive a scanned image of the first document (e.g., the health insurance document 124 used for illustrative purposes only) via a scanner 114 associated with the provider application 112. In an example, the scanner 114 may be scanning software. In another example, the scanner 114 may be a personal or commercial hardware scanning device.

The first document (e.g., the health insurance document 124) may be a paper document used as part of an overall transaction. The first document (e.g., the health insurance document 124) may include any physical representation of handwritten, typewritten or printed text. The scanned image of the first document (e.g., the health insurance document 124) may include any image that results from the scanning of a document. For example, the scanned image of the first document (e.g., the health insurance document 124) may include a JPEG image, a bitmap image, a TIFF image, a RAW image, etc. However, it should be appreciated that the scanned image of the first document (e.g., the health insurance document 124) may include any image type.

The provider application 112 may then transfer the image of the first document (e.g., the health insurance document 124) to the verification system 126 for processing. The verification system 126 is configured to: receive the image of the first document (e.g., the health insurance document 124) from the provider application 112 and store the image of the first document (e.g., the health insurance document 124) in the storage 144. In examples, the verification system 126 may process the image of the first document (e.g., the health insurance document 124) via the OCR mechanism 120 and/or the image processing mechanism 116. It should be appreciated that, as described herein, the OCR mechanism 120 includes any mechanical or electronic translation of the scanned image of the first document (e.g., the health insurance document 124) into machine-editable text by targeting one glyph or character at a time. In other examples, instead of the OCR processing, QR code, barcode, or machine readable zone (MRZ) reading may occur.

It should be appreciated that the image processing mechanism 116 may include: optical word recognition (that targets typewritten text, one word at a time for languages that use a space as a word divider), intelligent character recognition (that targets handwritten print script or cursive text one glyph at a time, usually involving machine learning mechanisms) and/or intelligent word recognition (that targets handwritten print script or cursive text, one word at a time, which may be used for languages where glyphs are not separated in cursive script), or any other sort of image processing mechanism 116 known to those having ordinary skill in the art.

The OCR processing may not need to be performed in particular circumstances. For example, the OCR processing need not occur if the first document (e.g., the health insurance document 124) is an electronic document.

Performing the OCR on the image of the first document (e.g., the health insurance document 124) includes: (1) pre-processing the first document (e.g., the health insurance document 124) to improve the chances of successful recognition, (2) utilizing one or more text recognition algorithms on the image of the first document (e.g., the health insurance document 124), and/or (3) post-processing the first document (e.g., the health insurance document 124).

The pre-processing stage may occur via one or more machine learning algorithms and/or artificial intelligence algorithms, among others, which will be discussed in turn. The algorithms of this pre-processing stage are not limited to any particular algorithms. The pre-processing stage may de-skew the first document (e.g., the health insurance document 124) by tilting the image of the first document (e.g., the health insurance document 124) a few degrees clockwise or counterclockwise in order to make lines of text perfectly horizontal or vertical. The pre-processing stage may also despeckle the image of the first document (e.g., the health insurance document 124) by removing positive and negative spots and smoothing edges. The pre-processing stage may further include binarisating the image of the first document (e.g., the health insurance document 124) to convert the image of the first document (e.g., the health insurance document 124) from color or greyscale to black-and-white (e.g., a binary image). The task of binarisation is performed to separate the text (or any other desired image component) from the background and is necessary since most commercial recognition algorithms work only on binary images since it proves to be simpler to do so.

The pre-processing stage may additionally include cleaning up non-glyph boxes and lines in the image of the first document (e.g., the health insurance document 124), zoning the image of the first document (e.g., the health insurance document 124) (e.g., identifying columns, paragraphs, captions, etc. as distinct blocks), detecting lines and words in the image of the first document (e.g., the health insurance document 124), recognizing script in the image of the first document (e.g., the health insurance document 124), isolating or segmenting characters in the image of the first document (e.g., the health insurance document 124), normalizing the image of the first document (e.g., the health insurance document 124), cropping the image of the first document (e.g., the health insurance document 124), and/or reducing noise for the first document (e.g., the health insurance document 124). It should be appreciated that the pre-processing stage may include one or more of the previous tasks/processes and/or additional tasks/processes not explicitly described herein.

The one or more text recognition algorithms may include a matrix matching algorithm and/or a feature extraction algorithm, among others. As described herein, "matrix matching" (or pattern matching, pattern recognition, or image correlation) involves comparing an image to a stored glyph on a pixel-by-pixel basis, relying on the input glyph being correctly isolated from the rest of the image, and on the stored glyph being in a similar font and at the same scale. This technique works best with typewritten text.

As described herein, "feature extraction" involves decomposing glyphs into "features" like lines, closed loops, line direction, and line intersections. The extraction features reduces the dimensionality of the representation and makes the recognition process computationally efficient. These features are compared with an abstract vector-like representation of a character, which might reduce to one or more glyph prototypes.

The performance of the OCR on the image of the first document (e.g., the health insurance document 124) also includes a post-processing stage. Such post-processing of the first document (e.g., the health insurance document 124) includes identifying one or more OCR errors in the first document (e.g., the health insurance document 124) and correcting those errors, which will be discussed in turn.

The verification system 126 is further configured to: extract a patient identifier (e.g., a first patient identifier 134 associated with the patient 102) from the first document (e.g., the health insurance document 124). The first patient identifier 134 is associated with the patient 102 and may be any sort of identifier from the first document (e.g., the health insurance document 124) that could be used for identification purposes. For example, the first patient identifier 134 may include a purchase order number, a heading of a document, a title of a document, a file name, an alphanumeric identifier, a number, a string of characters, a string of numbers (e.g., the last four numbers of a patients' social security number), etc.

In other examples, the first patient identifier 134 may be manually extracted from the first document. In further examples, the first patient identifier 134 may be obtained and/or input from another source, such as from the patient 102, a third-party, from scanning a code on the first document (e.g., the health insurance document 124), etc.

The verification system 126 is further configured to compare the patient identifier (e.g., the first patient identifier 134) to content in a database/repository (e.g., the third-party insurer database 128 and/or the healthcare provider database 130, among others) to identify a second document related to the first document (e.g., the health insurance document 124). As described herein "related" means that the first document is in some way associated with or connected to the second document. For example, the second document may include an invoice for a healthcare provider appointment related to the first document, which is the health insurance document 124, that was used to reduce payment for the healthcare provider appointment. In some instances, the first document (e.g., the health insurance document 124) and the second document share the patient identifier (e.g., the first patient identifier 134).

As shown in FIG. 1A and FIG. 1B, the third-party insurer database 128 may include documents, such as a first claim 136 and a second claim 138. The first claim 136 is associated with the first patient identifier 134 (of the patient 102) and the second claim 138 is associated with a second patient identifier 140 (of another patient/user). In this example, the verification system 126 may compare the patient identifier (e.g., the first patient identifier 134 associated with the patient 102) to content (e.g., the first claim 136 and the second claim 138) in the third-party insurer database 128 to identify the second document (e.g., the first claim 136) related to the first document (e.g., the health insurance document 124) and sharing the patient identifier (e.g., the first patient identifier 134) with the first document (e.g., the health insurance document 124).

The verification system 126 is further configured to: verify/validate (e.g., via the validation mechanism 118) the first document (e.g., the health insurance document 124) and the second document (e.g., the first claim 136) as being associated with the patient based on the comparison and predefined business rules. The predefined business rules may be any rules related to the first document and/or the second document. For example, the verification system 126 may verify/validate the first document (e.g., the health insurance document 124) and the second document (e.g., the first claim 136) as being associated with the patient 102, as these documents share the patient identifier (e.g., the first patient identifier 134) with the patient 102.

Moreover, the verification system 126 is configured to: utilize a weighted average mechanism to assign a confidence score to the match between the first document (e.g., the health insurance document 124) and the second document (e.g., the first claim 136). In response to having a match percentage above a predetermined percentage, the verification system 126 validates that the first document (e.g., the health insurance document 124) is related to the second document (e.g., the first claim 136).

In additional examples, the post-processing of the first document (e.g., the health insurance document 124) may include correcting the one or more OCR errors in the first document (e.g., the health insurance document 124) using the content from the second document (e.g., the first claim 136). For example, textual information may be missing from the first document (e.g., the health insurance document 124). Upon verifying that the second document (e.g., the first claim 136) relates to the first document (e.g., the health insurance document 124), the verification system 126 may fill the missing information of the first document (e.g., the health insurance document 124) with information from the second document (e.g., the first claim 136).

As another example, a term in the first document (e.g., the health insurance document 124) may be correlated to a different term in the second document (e.g., the first claim 136) that refers to the same thing, which may result in an OCR error. In another embodiment, a closest match may be determined for a given term in the first document (e.g., the health insurance document 124) if no direct correlation can be found. In other examples, the verification system 126 may generate an alert and transmit the alert to the provider application 112 (of FIG. 1A), a website 142 (of FIG. 1B), the third-party insurer database 128, the healthcare provider database 130, another database, and/or to the computing device 104 for human reconciliation of the one or more OCR errors. Such alert may occur via a notification or a message.

In response to having the match percentage below the predetermined percentage, the verification system 126 may fail to verify that the first document (e.g., the health insurance document 124) is related to the second document (e.g., the first claim 136), may generate an alert, and may transmit the alert to a human for reconciliation. The alert may be any type of alert and may include audio, text, graphics, and/or video. In other examples, the alert may be transmitted to the provider application 112, the website 142 (of FIG. 1B), the third-party insurer database 128, the healthcare provider database 130, another database, and/or to the computing device 104.

As shown in FIG. 1B, the provider application 112 may be replaced with a provider website 142 that the patient 102 may access using the GUI 106 via the Internet. The website 142 is configured to receive the image of the first document via scanning software.

In an illustrative example, the first document may comprise the health insurance document 124 and the verification system 126 may transmit an inquiry to the third-party insurer database 128, the healthcare provider database 130, and/or another database/repository to confirm a status of health insurance benefits associated with the health insurance document 124. The status of the health insurance benefits associated with the health insurance document 124 may be a current status or an expired status.

If the verification system 126 confirms the status of the health insurance benefits associated with the health insurance document 124 as being current, the verification system 126 may reduce a total cost for a healthcare appointment of the patient 102 based on the health insurance benefits associated with the health insurance document 124 in real-time. The verification system 126 may also transmit the modified payment to the provider application 112 or the website 142, prompt the patient 102 to pay the modified payment, receive the payment, and process the payment. If the verification system 126 confirms the status of the health insurance benefits associated with the health insurance document 124 as being expired, the verification system 126 may not reduce the payment for the healthcare appointment of the patient 102.

In further examples, the verification system 126 is configured to: utilize the weighted average mechanism described herein to assign the confidence score to information extracted from the first document (e.g., the health insurance document 124) and/or the second document (e.g., the first claim 136) and/or the information input by the patient 102. For example, the verification system 126 may extract a patient street address from the first document, the patient street address from the second document, and the patient 102 may input their street address. The verification system 126 may compare the street address information of the first document (e.g., the health insurance document 124), the second document (e.g., the first claim 136), and the information input by the patient 102. The verification system 126 may assign a confidence score based on the comparison. If the information matches, the confidence score will be higher than if the information does not match.

As a first illustrative example, the first document (e.g., the health insurance document 124) and/or the second document (e.g., the first claim 136) may include the following street address for the patient 102: Wallaeby Way. The patient 102 may have inputted the following street address: Wallaeby Way. Since the street addresses match, the confidence score will be high.

As a second illustrative example, the first document (e.g., the health insurance document 124) and/or the second document (e.g., the first claim 136) may include the following last name for the patient 102: Smith. The patient 102 may have inputted the following last name: Smithe on accident. Since the last name of the patient is misspelled, the confidence score will be lower than in the first illustrative scenario.

The verification system 126 may generate the alert based on the confidence score and may transmit the alert to the provider application 112 (of FIG. 1A), the website 142 (of FIG. 1B), the third-party insurer database 128, the healthcare provider database 130, another database, and/or to the computing device 104 for display.

It should be appreciated that the confidence score described herein will be measured and displayed via any means, such as a percentage, a fraction, a graphic, etc. Moreover, it should be appreciated that the data/information may be transmitted using encrypted or secure transfer methods to protect privacy of the patient 102.

The system of FIG. 1A and FIG. 1B allows for the patient 102 to pre-register of any necessary identification data (e.g., a driver's license, a health insurance card, demographic data, etc.), confirm that the health insurance coverage is valid on the date of service, confirm of any patient payment responsibility, and confirm or authorize of any referral requirements prior to the patient 102 attending the healthcare appointment.

Figure 2:
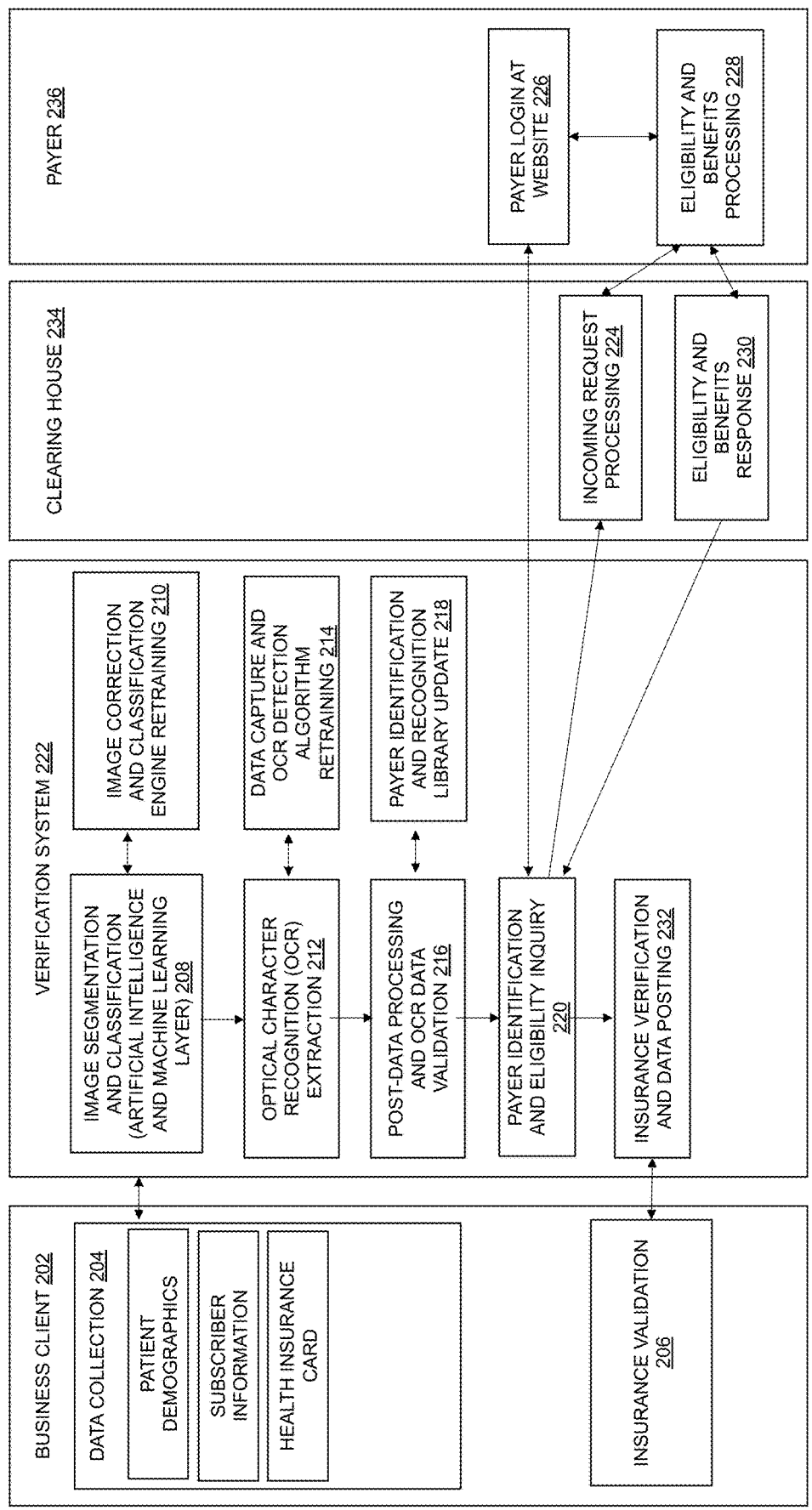
FIG. 2 depicts a schematic diagram of a system to verify documentation in real-time utilizing artificial intelligence (AI), optical character recognition (OCR), and machine learning (ML), according to at least some embodiments disclosed herein.

FIG. 2 depicts a schematic diagram of a system to verify documentation in real-time utilizing artificial intelligence (AI), optical character recognition (OCR), and machine learning (ML), according to at least some embodiments disclosed herein.

The system of FIG. 2 includes numerous components, such as a business client 202, a verification system 222, a clearing house 234, and/or a payer 236 (or patient). The business client 202 may collect data (e.g., data collection component 204), such as patient demographic and healthcare subscriber information, among other information, as well as capture at least one image of a health insurance card. This information is transmitted to the verification system 222.

The verification system 222, in a process step 208, may utilize an AI and/or machine learning layer to engage in image segmentation and classification. A process step 210 follows the process step 208 and includes image correction and classification, as well as retraining of the verification system 222. Next, the verification system 222 is configured to perform content extraction via the OCR at a process step 212. It should be appreciated that instead of OCR, QR code, barcode, or machine readable zone (MRZ) reading may occur.

Then, a process step 214 follows the process step 212 and includes retraining of a data capture and OCR detection algorithm at a process step 214. A process step 216 follows and incudes the verification system 222 engaging in post-data processing and OCR data validation. A process step 218 follows the process step 216 and includes updating payer identification and in the repository/database. Then, a process step 220 occurs, which includes the verification system 222 identifying the payer and engaging in an insurance eligibility inquiry.

A process step 224 and a process step 226 follow the process step 220. The process step 224 includes the clearing house 234 receiving an incoming request and processing the request. The process step 226 includes the payer 236 logging in at a website. Next, a process step 228 follows the process step 226 and includes processing eligibility and benefit information for the patient.

Then, the process step 224 and a process step 230 follows the process step 228. The process step 230 includes the clearing house 234 creating an eligibility and benefits response. The eligibility and benefits response of the process step 230 is then transmitted to the verification system 222. Next, the verification system 222 engages in insurance verification and data posting at a process step 232. Insurance validation then occurs at a process step 206 at the business client 202.

Figure 3:
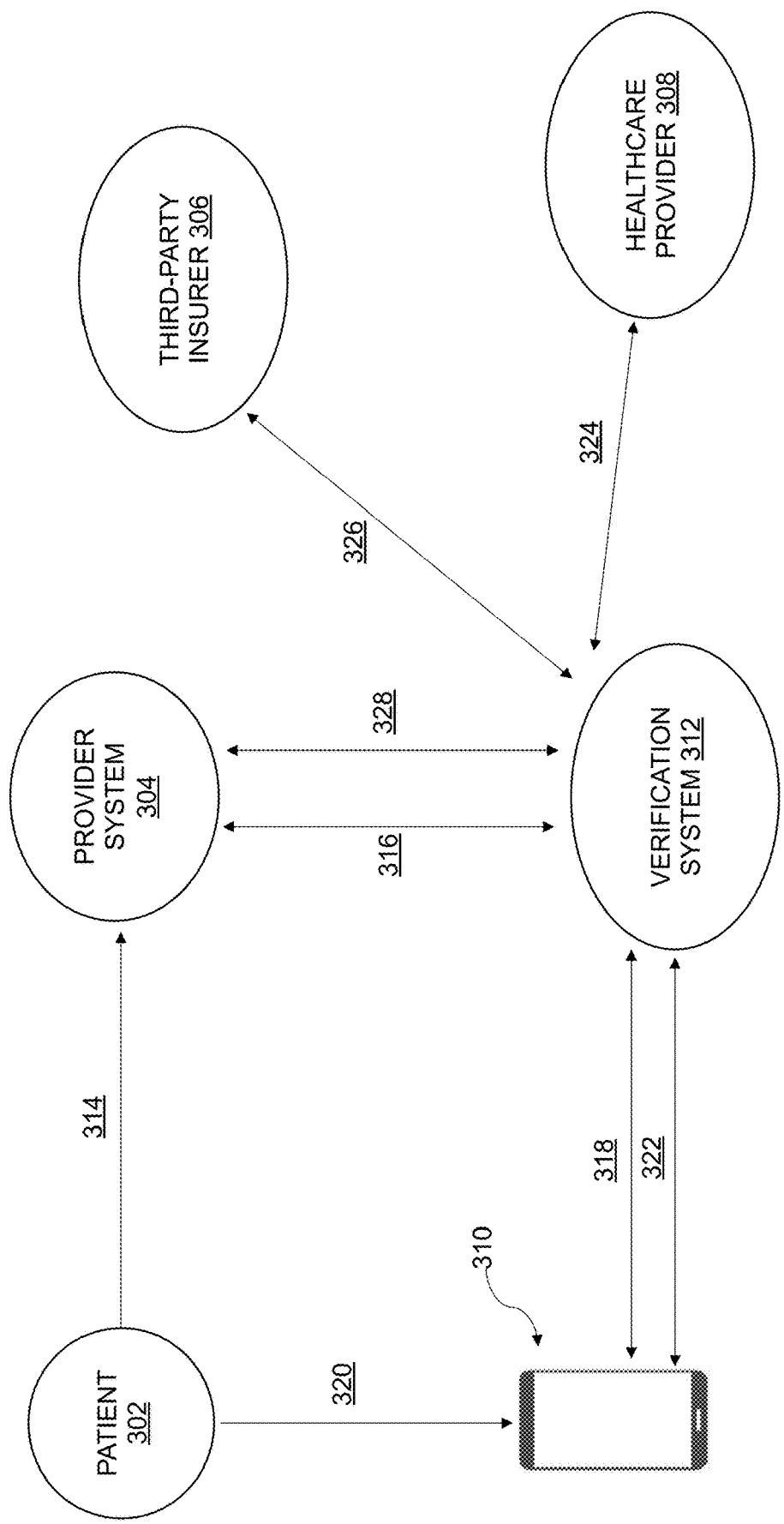
FIG. 3 depicts a schematic diagram of a method executed on a computing device to verify documentation in real-time, according to at least some embodiments disclosed herein.

FIG. 3 depicts a schematic diagram of a method executed on a computing device to verify documentation in real-time, according to at least some embodiments disclosed herein.

As shown in FIG. 3, a patient 302, at a process step 314, visits a website of a provider system 304 to make a healthcare appointment. Next, the patient, appointment, and other information is transmitted via a process step 316 to a verification system 312 via web services. Then, the verification system 312 sends a link, SMS, or email message to a computing device 310 associated with the patient 301 at a process step 318. The patient 302 engages the computing device 310 to open the link, SMS, or email message and input the requested information, at a process step 320. The computing device 310 captures information and transmits the information to the verification system 312 at a process step 322.

The verification system 312 then corrects and handles OCR exceptions at a process step 324 with a front desk/human at a healthcare providers office 308. The verification system 312 also verifies insurance and eligibility benefits of the patient 302, at a process step 326, with a third-party insurer or a third-party insurer database 306. Lastly, the verification system 312 transfers, via a process step 328, information, such as insurance information, benefit information, etc., using web services to the provider system 304.

Figure 4:
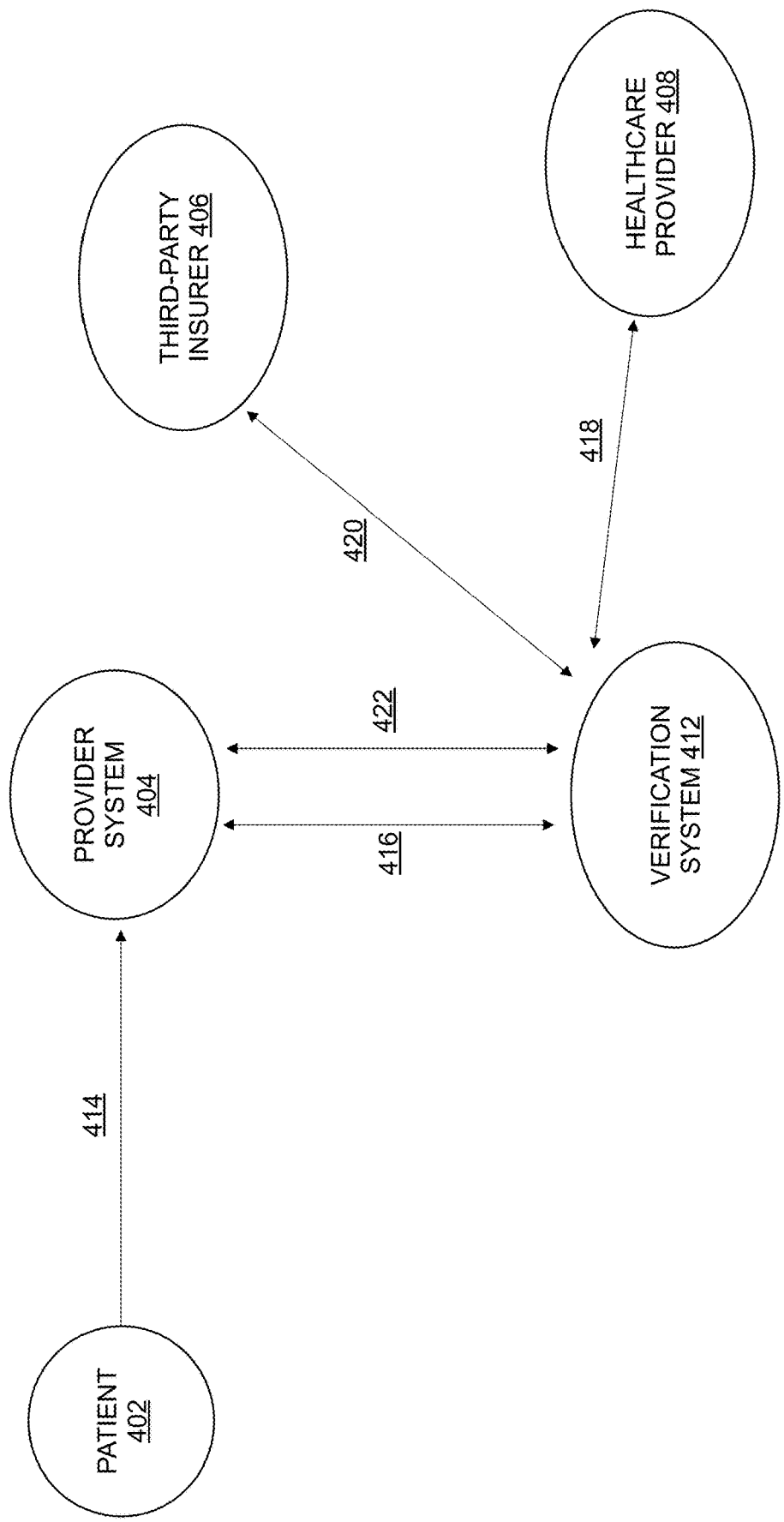
FIG. 4 depicts a schematic diagram of a method executed on a website to verify documentation in real-time, according to at least some embodiments disclosed herein.

FIG. 4 depicts a schematic diagram of a method executed on a website to verify documentation in real-time, according to at least some embodiments disclosed herein.

As shown in FIG. 4, a patient 402, at a process step 414, visits a healthcare providers website of a provider system 404 to make a healthcare appointment. Next, at a process step 416, the provider website of the provider system 404 uses an embedded webform to capture information of the patient 402 and then transmits such information to a verification system 412. Then, the verification system 412 corrects and handles OCR exceptions at a process step 418 with a front desk/human at a healthcare providers office 408. The verification system 412 also verifies insurance and eligibility benefits of the patient 402 at a process step 420 with a third-party insurer or a third-party insurer database 406. Lastly, the verification system 412 transfers, via a process step 422, information, such as insurance information, benefit information, etc., using web services to the provider system 404.

Figure 5:
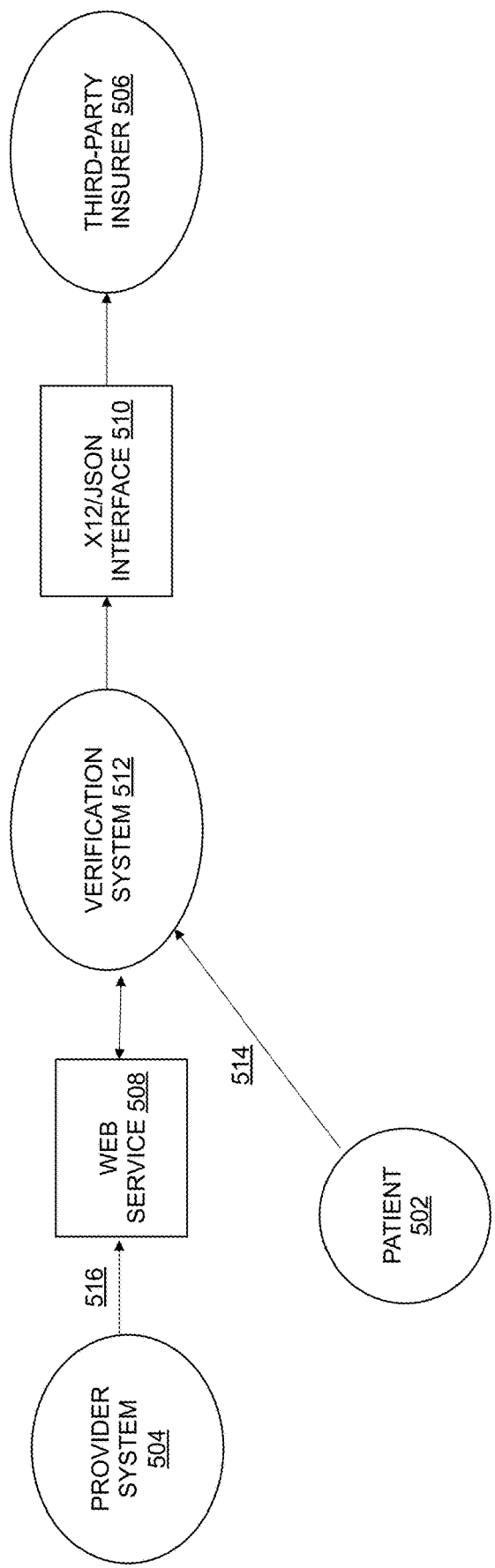
FIG. 5 and FIG. 6 depict schematic diagrams of data flow for methods to verify documentation in real-time, according to at least some embodiments disclosed herein.
Figure 6:
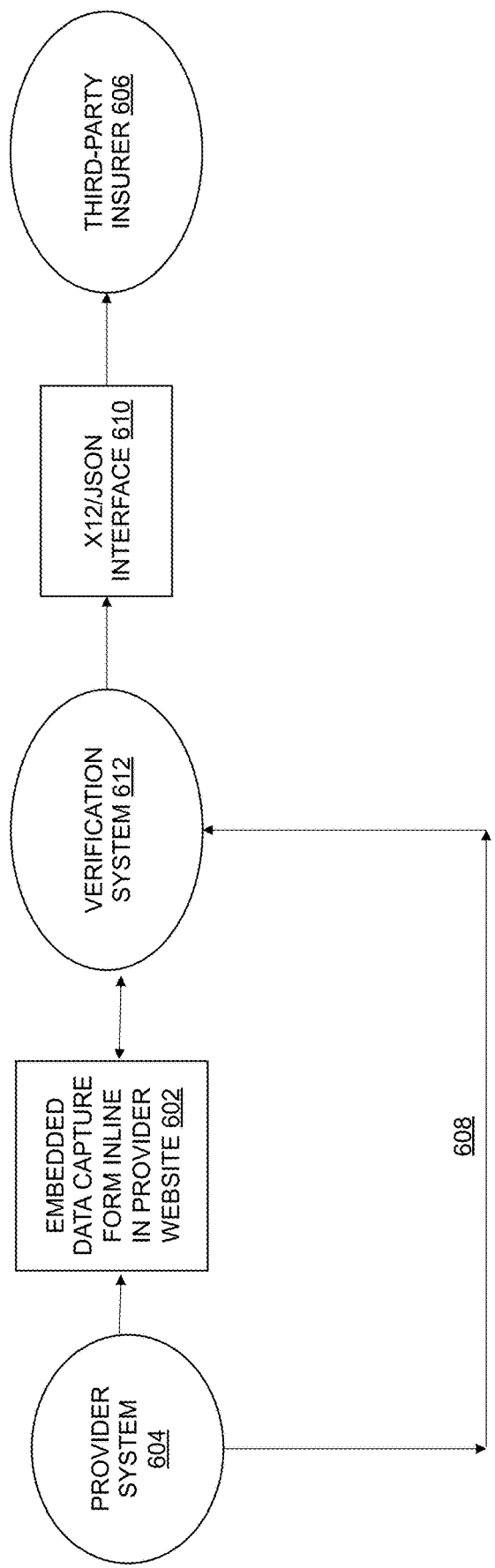

FIG. 5 and FIG. 6 depict schematic diagrams of a data flow for a method to verify documentation in real-time, according to at least some embodiments disclosed herein.

As shown in FIG. 5, a first data flow for the method to verify the documentation in real-time is depicted. In FIG. 5, a provider system 504 sends a patient 502 a message regrading a scheduled appointment. Such message may be sent by any means. Web services 508 of the provider system 504 receives, via a process step 516, information (e.g., health insurance card information, data, benefits) and transmits such information to a verification system 512. An X12/JSON interface 510 is used between the verification system 512 and a third-party insurer 506. The patient 502 may also send an email/SMS message to the verification system 512 that includes information via a process step 514.

As shown in FIG. 6, a second data flow for the method to verify the documentation in real-time is depicted. In FIG. 6, a provider system 604 provides a website that includes an embedded data capture form inline to which a patient can input information, as shown in a process step 602. Such information is transmitted to a verification system 612. A X12/JSON interface 610 is used between the verification system 612 and a third-party insurer 606. A web service of the provider system 604 is configured to transmit information between the verification system 612 and the provider system 604 at a process step 608.

Figure 7:
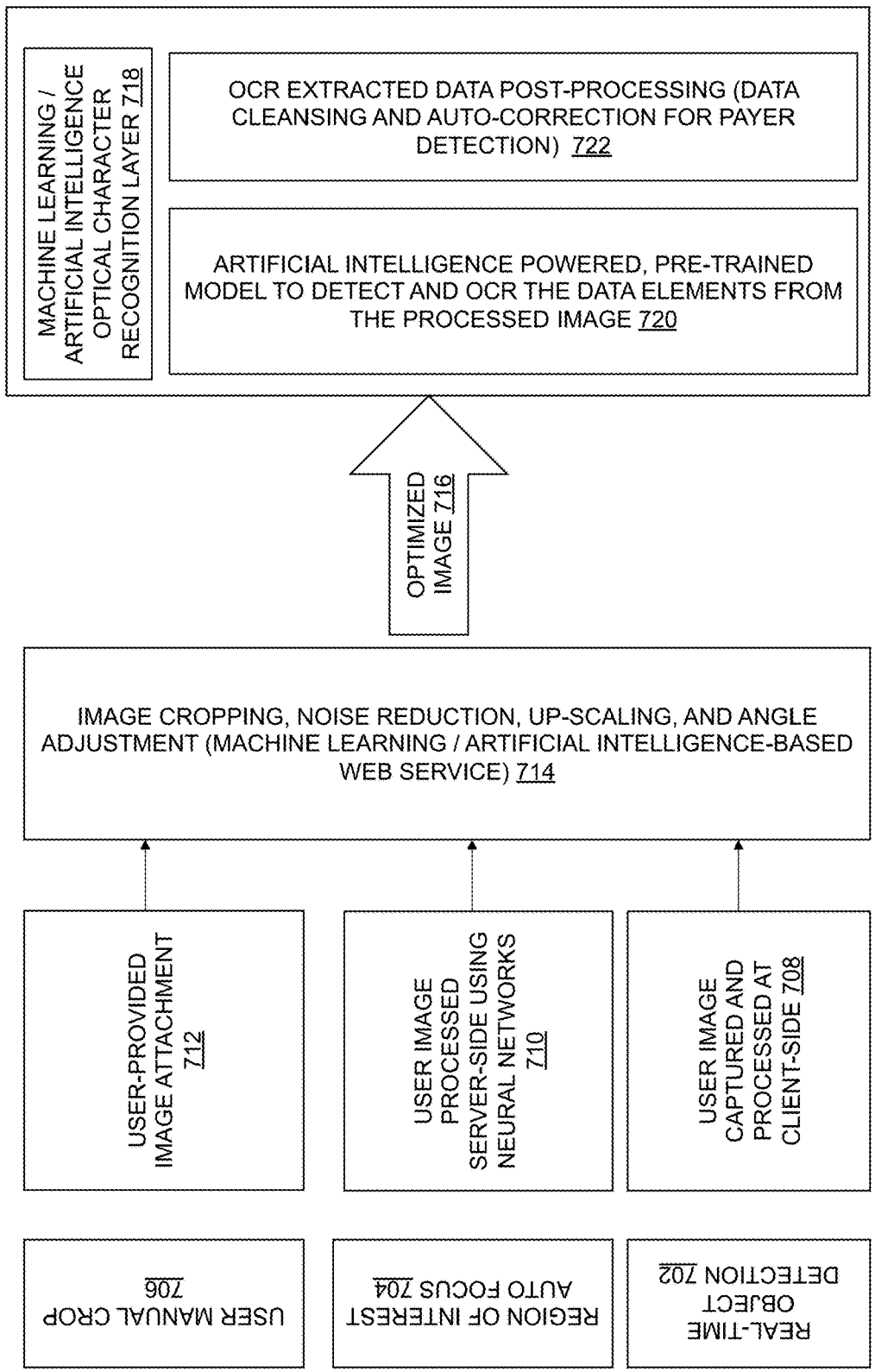
FIG. 7 depicts a schematic diagram of a framework to verify documentation in real-time utilizing AI, OCR, and/or ML, according to at least some embodiments disclosed herein.

FIG. 7 depicts a schematic diagram of a framework to verify documentation in real-time utilizing AI, OCR, and ML, according to at least some embodiments disclosed herein.

As shown in FIG. 7, the framework to verify documentation in real-time utilizing AI, OCR, and ML includes: (1) real-time object detection 702, (2) region of interest auto focus 704, and (3) user manual cropping 706. The system described herein first engages in the real-time object detection 702 to capture a user image (e.g., of a healthcare document, such as a healthcare insurance card) and process the image at a client-side of the system at a process step 708. Next, the system described engages in region of interest auto focus 704 to process the user image server-side using neural networks at a process step 710. Then, the system engages in user manual cropping 706 where the user-provided image is cropped and/or further processed at a process step 712.

Then, the system engages in a process step 714 that includes image cropping, noise reduction, up-scaling, and angle adjustment using one or more ML and/or AI-based algorithms or web services. As a result of the process step 714, the image is optimized as image 716. The optimized image (e.g., the image 716) is then transmitted to a ML/AI-OCR layer 718. At the ML/AI-OCR layer 718, the system is configured to: (1) at a process step 720, utilize an artificial intelligence powered, pre-trained model to detect and OCR the data elements from the processed image (e.g., the optimized image 716) and (2) at a process step 722, engage in OCR extracted data post-processing (e.g., data cleansing and auto-correction for payer detection).

Figure 8:
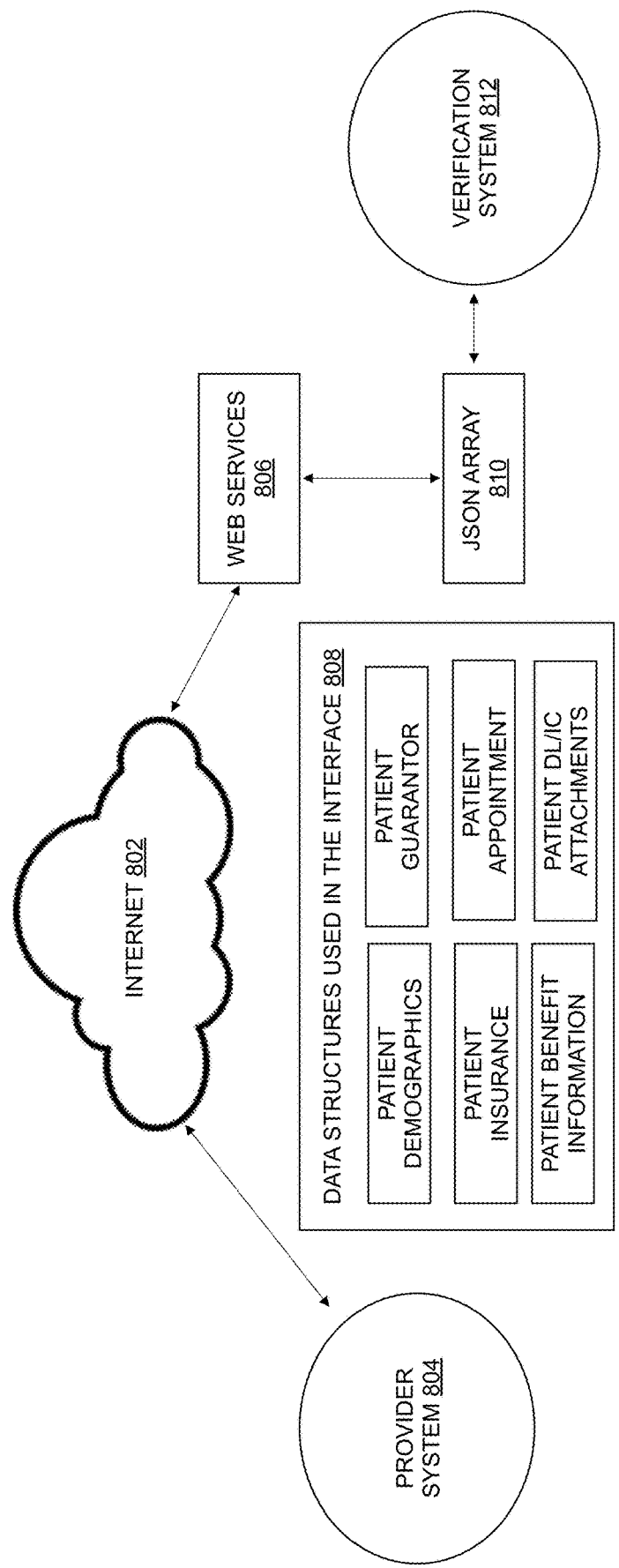
FIG. 8 depicts a schematic diagram of a healthcare provider interface used in a method to verify documentation in real-time, according to at least some embodiments disclosed herein.

FIG. 8 depicts a schematic diagram of a healthcare provider interface used in a method to verify documentation in real-time, according to at least some embodiments disclosed herein.

As shown in FIG. 8, a provider system 804 interacts via the Internet 802 with web services 806. Web services 806, in turn, utilizes a JSON array 810 to interact with a verification system 812. Data structures used in the healthcare provider interface 806 include, but are not limited to, patient demographics, patient guarantor information, patient insurance information, patient appointment information, patient benefit information, patient attachments, etc.

Figure 9:
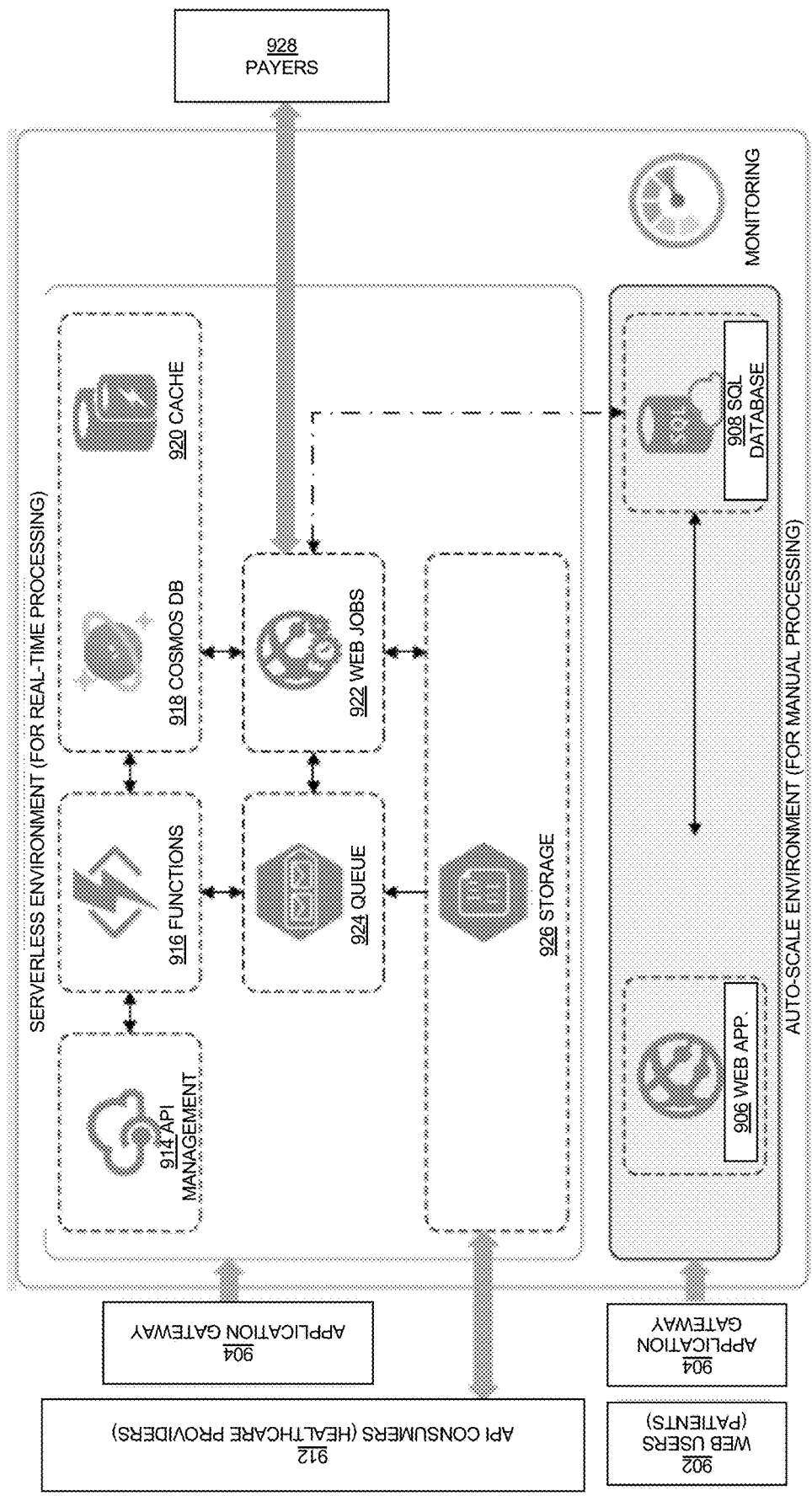
FIG. 9 depicts a schematic diagram of cloud architecture of a system for verifying documentation in real-time, according to an embodiment of the present invention.

FIG. 9 depicts a schematic diagram of cloud architecture of a system for verifying documentation in real-time, according to an embodiment of the present invention.

As shown in FIG. 9, the cloud architecture of the system includes an auto-scale environment and a serverless environment. The auto-scale environment may be used for manual processing of information and the serverless environment may be used for real-time processing of information. Web-users/patients 902 may utilize an application gateway 904 to access a web application 906 of the auto-scale environment. The web application 906 may interact with an SQL database 908 of the auto-scale environment.

API consumers (e.g., healthcare providers) 912 may utilize the application gateway 904 to access the serverless environment. The serverless environment may include numerous modules or engines, such as a storage engine 926, an API management engine 914, a functions engine 916, a queue engine 924, and/or a web jobs engine 922, among others. The serverless environment may also include a cosmos database 918 and/or a cache 920. The SQL database 908 and/or payers (e.g., insurance providers) 928 may interact with one or more engines of the serverless environment.

The verification system (e.g., the verification system 126 of FIG. 1A and FIG. 1B, the verification system 222 of FIG. 2, the verification system 312 of FIG. 3, the verification system 412 of FIG. 4, the verification system 512 of FIG. 5, the verification system 612 of FIG. 6, and/or the verification system 812 of FIG. 8) described herein provides numerous benefits to the patient (e.g., the patient 102 of FIG. 1A and FIG. 1B, the patient 302 of FIG. 3, the patient 402 of FIG. 4, and/or the patient 502 of FIG. 5), the healthcare provider, and the office staff of the healthcare providers office (e.g., the healthcare providers office 308 of FIG. 3 and/or the healthcare providers office 408 of FIG. 4).

For example, the verification system provides at least the following benefits to the patient: allows the patient easily and contactlessly "check-in" for a healthcare appointment from anywhere to reduce the risk of exposure to COVID-19 and similar diseases/illnesses, allows the patient to understand the financial cost and responsibility of a healthcare appointment prior to receiving the services of the healthcare appointment, and easily saves and stores information of the patient such that the patient need not carry his/her health insurance card and other identifying documentation. The verification system provides at least the following benefits to the healthcare provider: reduces administrative workload for greater productivity and cost savings, allows for accurate data capture and digital insurance verification for faster claims processing, and reduces the number of administrative errors and turnover. Further, the verification system provides at least the following benefits to the office staff of the healthcare providers office: reduces the risk of exposure to COVID-19 and similar diseases/illnesses through the contactless exchange of documentation and payments and reduces mistakes and reworking of healthcare claims from misreading healthcare insurance cards. As such, the verification system described herein allows for real-time and automated insurance eligibility verification, providing numerous benefits to the patient, the healthcare provider, and the office staff of the healthcare providers office.

Figure 10:
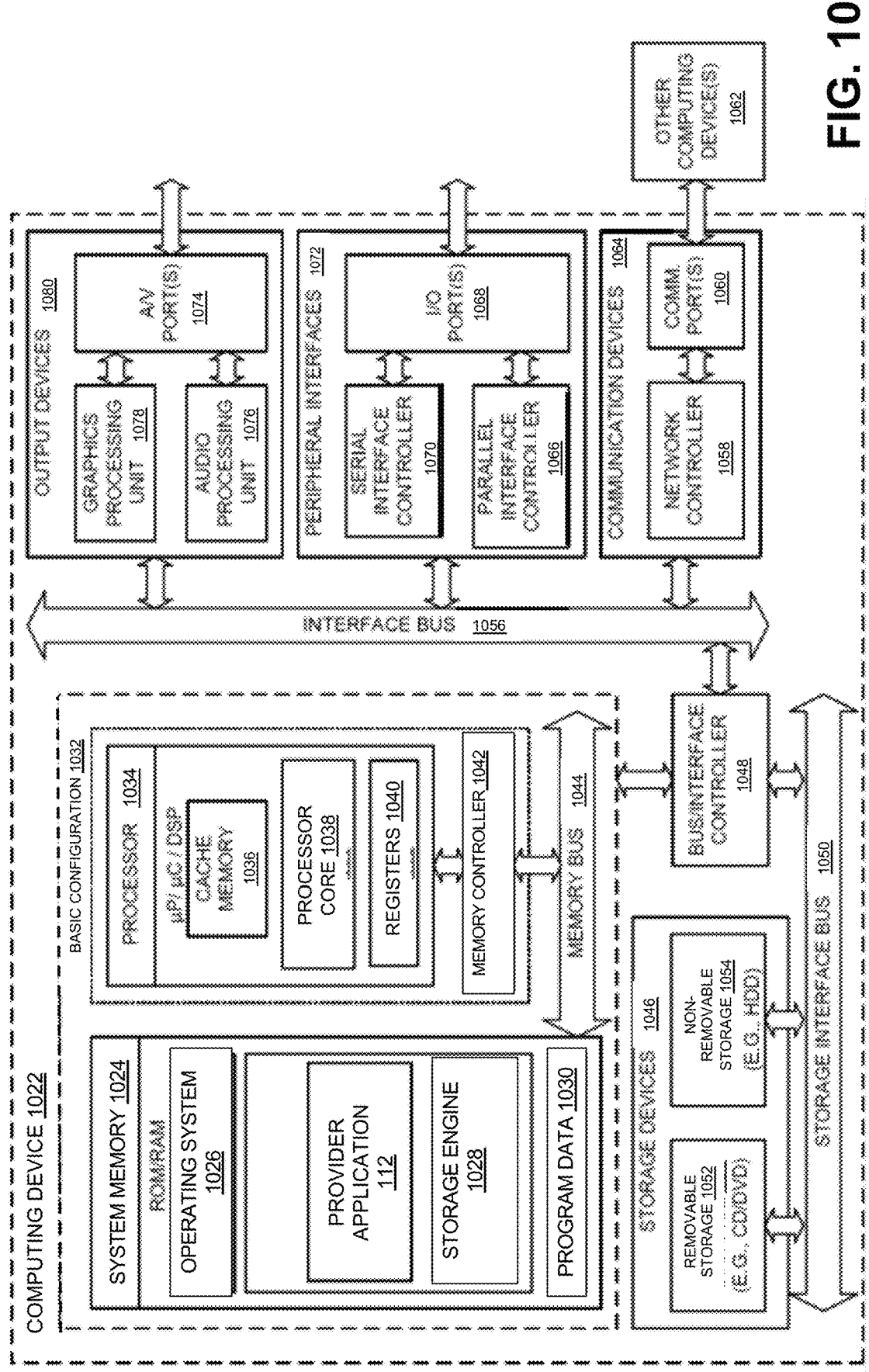
FIG. 10 depicts a block diagram of a computing device included within a computer system that is configured to implement a method for verifying documentation in real-time, in accordance with embodiments of the present invention.

FIG. 10 depicts a block diagram of a computing device included within a computer system that is configured to implement a method for verifying documentation in real-time, in accordance with embodiments of the present invention.

In some embodiments, the present invention may be a computer system, a method, and/or the computing device 104 (of FIG. 1A and FIG. 1B) or the computing device 1022 (of FIG. 10). For example, the computer system and/or the computing device 1022 may be utilized to implement a method for verifying documentation in real-time.

A basic configuration 1032 of a computing device 1022 is illustrated in FIG. 10 by those components within the inner dashed line. In the basic configuration 1032 of the computing device 1022, the computing device 1022 includes a processor 1034 and a system memory 1024.

In some examples, the computing device 1022 may include one or more processors and the system memory 1024. A memory bus 1044 is used for communicating between the one or more processors 1034 and the system memory 1024.

Depending on the desired configuration, the processor 1034 may be of any type, including, but not limited to, a microprocessor (µP), a microcontroller (µC), and a digital signal processor (DSP), or any combination thereof. Further, the processor 1034 may include one more levels of caching, such as a level cache memory 1036, a processor core 1038, and registers 1040, among other examples. The processor core 1038 may include an arithmetic logic unit (ALU), a floating point unit (FPU), and/or a digital signal processing core (DSP Core), or any combination thereof. A memory controller 1042 may be used with the processor 1034, or, in some implementations, the memory controller 1042 may be an internal part of the memory controller 1042.

Depending on the desired configuration, the system memory 1024 may be of any type, including, but not limited to, volatile memory (such as RAM), and/or non-volatile memory (such as ROM, flash memory, etc.), or any combination thereof. The system memory 1024 includes an operating system 1026, one or more engines, such as the provider application 112, and program data 1030. In some embodiments, the provider application 112 may be an application, a software program, a service, or a software platform, as described infra. The system memory 1024 may also include a storage engine 1028 that may store any information disclosed herein.

Moreover, the computing device 1022 may have additional features or functionality, and additional interfaces to facilitate communications between the basic configuration 1032 and any desired devices and interfaces. For example, a bus/interface controller 1048 is used to facilitate communications between the basic configuration 1032 and data storage devices 1046 via a storage interface bus 1050. The data storage devices 1046 may be one or more removable storage devices 1052, one or more non-removable storage devices 1054, or a combination thereof. Examples of the one or more removable storage devices 1052 and the one or more non-removable storage devices 1054 include magnetic disk devices (such as flexible disk drives and hard-disk drives (HDD)), optical disk drives (such as compact disk (CD) drives or digital versatile disk (DVD) drives), solid state drives (SSD), and tape drives, among others.

In some embodiments, an interface bus 1056 facilitates communication from various interface devices (e.g., one or more output devices 1080, one or more peripheral interfaces 1072, and one or more communication devices 1064) to the basic configuration 1032 via the bus/interface controller 1056. Some of the one or more output devices 1080 include a graphics processing unit 1078 and an audio processing unit 1076, which are configured to communicate to various external devices, such as a display or speakers, via one or more A/V ports 1074.

The one or more peripheral interfaces 1072 may include a serial interface controller 1070 or a parallel interface controller 1066, which are configured to communicate with external devices, such as input devices (e.g., a keyboard, a mouse, a pen, a voice input device, or a touch input device, etc.) or other peripheral devices (e.g., a printer or a scanner, etc.) via one or more I/O ports 1068.

Further, the one or more communication devices 1064 may include a network controller 1058, which is arranged to facilitate communication with one or more other computing devices 1062 over a network communication link via one or more communication ports 1060. The one or more other computing devices 1062 include servers, the database, mobile devices, and comparable devices.

The network communication link is an example of a communication media. The communication media are typically embodied by the computer-readable instructions, data structures, program modules, or other data in a modulated data signal, such as a carrier wave or other transport mechanism, and include any information delivery media. A "modulated data signal" is a signal that has one or more of its characteristics set or changed in such a manner as to encode information in the signal. By way of example, and not limitation, the communication media may include wired media (such as a wired network or direct-wired connection) and wireless media (such as acoustic, radio frequency (RF), microwave, infrared (IR), and other wireless media). The term "computer-readable media," as used herein, includes both storage media and communication media.

It should be appreciated that the system memory 1024, the one or more removable storage devices 1052, and the one or more non-removable storage devices 1054 are examples of the computer-readable storage media. The computer-readable storage media is a tangible device that can retain and store instructions (e.g., program code) for use by an instruction execution device (e.g., the computing device 1022). Any such, computer storage media is part of the computing device 1022.

The computer readable storage media/medium can be a tangible device that can retain and store instructions for use by an instruction execution device. The computer readable storage media/medium may be, for example, but is not limited to, an electronic storage device, a magnetic storage device, an optical storage device, an electromagnetic storage device, and/or a semiconductor storage device, or any suitable combination of the foregoing. A non-exhaustive list of more specific examples of the computer readable storage media/medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and/or a mechanically encoded device (such as punch-cards or raised structures in a groove having instructions recorded thereon), and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Aspects of the present invention are described herein regarding illustrations and/or block diagrams of methods, computer systems, and computing devices according to embodiments of the invention. It will be understood that each block in the block diagrams, and combinations of the blocks, can be implemented by the computer-readable instructions (e.g., the program code).

The computer-readable instructions are provided to the processor 1034 of a general purpose computer, special purpose computer, or other programmable data processing apparatus (e.g., the computing device 1022) to produce a machine, such that the instructions, which execute via the processor 1034 of the computer or other programmable data processing apparatus, create means for implementing the functions/acts specified in the block diagram blocks. These computer-readable instructions are also stored in a computer-readable storage medium that can direct a computer, a programmable data processing apparatus, and/or other devices to function in a particular manner, such that the computer-readable storage medium having instructions stored therein comprises an article of manufacture including instructions, which implement aspects of the functions/acts specified in the block diagram blocks.

The computer-readable instructions (e.g., the program code) are also loaded onto a computer (e.g. the computing device 1022), another programmable data processing apparatus, or another device to cause a series of operational steps to be performed on the computer, the other programmable apparatus, or the other device to produce a computer implemented process, such that the instructions, which execute on the computer, the other programmable apparatus, or the other device, implement the functions/acts specified in the block diagram blocks.

Computer readable program instructions described herein can also be downloaded to respective computing/processing devices from a computer readable storage medium or to an external computer or external storage device via a network (e.g., the Internet, a local area network, a wide area network, and/or a wireless network). The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer/computing device, partly on the user's computer/computing device, as a stand-alone software package, partly on the user's computer/computing device and partly on a remote computer/computing device or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to block diagrams of methods, computer systems, and computing devices according to embodiments of the invention. It will be understood that each block and combinations of blocks in the diagrams, can be implemented by the computer readable program instructions.

The block diagrams in the Figures illustrate the architecture, functionality, and operation of possible implementations of computer systems, methods, and computing devices according to various embodiments of the present invention. In this regard, each block in the block diagrams may represent a module, a segment, or a portion of executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block and combinations of blocks can be implemented by special purpose hardware-based systems that perform the specified functions or acts or carry out combinations of special purpose hardware and computer instructions.

Another embodiment of the invention provides a method that performs the process steps on a subscription, advertising, and/or fee basis. That is, a service provider can offer to assist in the method steps of verifying documentation in real-time. In this case, the service provider can create, maintain, and/or support, etc. a computer infrastructure that performs the process steps for one or more customers. In return, the service provider can receive payment from the customer(s) under a subscription and/or fee agreement, and/or the service provider can receive payment from the sale of advertising content to one or more third parties.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A system configured to verify documentation in real-time, the system comprising:
   a computing device;
   an application executable on the computing device, the application being configured to:
   receive an image of a first document from a patient; and
   transfer the image of the first document to a verification system; and the verification system being configured to:
   receive the image of the first document from the application;
   perform optical character recognition (OCR) on the image of the first document;
   extract a patient identifier and information from the first document, wherein the patient identifier is unique to a particular patient, and wherein the patient identifier comprises a combination of one or more of letters, words, and numbers;
   compare the patient identifier to content in a database, selected from a group consisting of a healthcare provider database and a third-party insurer database, to identify a second document related to the first document, and wherein the first document and the second document share the patient identifier;
   verify the first document and the second document as being associated with the patient based on the comparison and predefined business rules;
   compare the first document with the second document to obtain a match between the first document and the second document, wherein the match is a successful match when matching percentage between the first document and the second document is greater than a predetermined matching percentage; and
   identify one or more OCR errors in the first document, wherein identifying the one or more OCR errors include:
     identifying missing information from the first document; and
     determining a discrepancy in a correlation between a first term in the first document and a second term in the second document associated with same patient identifier as the first document, wherein the first term and the second term are different terms indicating a same concept;
   correcting the one or more OCR errors by:
     supplement the missing information in the first document from the second document, wherein the first document and the second document share same patient identifier; and
     associating the first term with the second term based on determination of a match percentage between the first term and the second term.

2. The system of claim 1, wherein each of the first document and the second document is selected from a group consisting of: an invoice, a receipt, a bill, a sales order document, an insurance claim document, a driver's license, a passport, an explanation of benefits document, and a medical insurance document.

3. The system of claim 1, wherein performance of the OCR on the image of the first document comprises:
   pre-processing the first document;
   utilizing one or more text recognition algorithms; and
   post-processing the first document.

4. The system of claim 3, wherein the pre-processing of the first document comprises: de-skewing the first document, cropping the image of the first document, reducing noise for the first document, de-speckling the first document, binarisating the first document, removing lines from the first document, analyzing a layout of the first document, detecting lines in the first document, detecting words in the first document, recognizing script in the first document, and/or isolating characters in the first document.

5. The system of claim 3, wherein the pre-processing of the first document occurs via one or more machine learning algorithms and artificial intelligence algorithms.

6. The system of claim 3, wherein each of the one or more text recognition algorithms are selected from a group consisting of: a matrix matching algorithm and a feature extraction algorithm.

7. The system of claim 1, wherein the verification system is further configured to:
   utilize a weighted average mechanism to assign a confidence score to the match between the first document and the second document.

8. A method executed by a system to verify documentation in real-time, the method comprising:
   receiving an image of a first document from a patient via a website associated with the system;
   receiving information from the patient via the website associated with the system;
   performing optical character recognition (OCR) on the image of the first document;
   extracting a patient identifier from the first document, wherein the patient identifier is unique to a particular patient, and wherein the patient identifier comprises a combination of one or more of letters, words, and numbers;
   comparing the patient identifier to content in a database, selected from a group consisting of a healthcare provider database and a third-party insurer database, to identify a second document related to the first document, and wherein the first document and the second document share the patient identifier;
   verifying the first document and the second document as being associated with the patient based on the comparison and predefined business rules;
   comparing the first document with the second document to obtain a match between the first document and the second document, wherein the match is a successful match when matching percentage between the first document and the second document is greater than a predetermined matching percentage; and identifying one or more OCR errors in the first document, wherein identifying the one or more OCR errors include:
  identifying missing information from the first document; and
  determining a discrepancy in a correlation between a first term in the first document and a second term in the second document associated with same patient identifier as the first document, wherein the first term and the second term are different terms indicating a same concept;
correcting the one or more OCR errors by:
  supplementing the missing information in the first document from the second document, wherein the first document and the second document share same patient identifier; and
  associating the first term with the second term based on determination of a match percentage between the first term and the second term.

9. The method of claim 8, wherein the first document comprises a medical insurance document, and wherein the method further comprises transmitting an inquiry to the database to confirm a status of health insurance benefits associated with the medical insurance document prior to the patient attending an appointment.

10. The method of claim 9, further comprising:
identifying the status of the health insurance benefits as being current; and
reducing a payment for the appointment based on the current status of the health insurance benefits in real-time.

11. The method of claim 10, further comprising:
transmitting a modified payment to the website for display to the patient;
prompting the patient to pay the modified payment via the website; and
in response to receiving the payment, processing the payment for the appointment.

12. The method of claim 8, wherein, in response to failing to verify the first document and the second document as being associated with the patient based on the comparison and predefined business rules, the method further comprises:
generating an alert; and
transmitting the alert to a human for reconciliation.

13. A computer system comprising one or more processors, one or more memories, and one or more computer-readable hardware storage devices, the one or more computer-readable hardware storage devices containing program code executable by the one or more processors via the one or more memories to implement a method to verify documentation in real-time, the method comprising:
receiving an image of a first document from a patient;
performing optical character recognition (OCR) on the image of the first document;
extracting a patient identifier and information from the first document, wherein the patient identifier is unique to a particular patient, and wherein the patient identifier comprises a combination of one or more of letters, words, and numbers;
comparing the patient identifier to content in a database, selected from a group consisting of a healthcare provider database and a third-party insurer database, to identify a second document related to the first document, and wherein the first document and the second document share the patient identifier;
verifying the first document and the second document as being associated with the patient based on the comparison and predefined business rules;
comparing the first document with the second document to obtain a match between the first document and the second document, wherein the match is a successful match when matching percentage between the first document and the second document is greater than a predetermined matching percentage;
utilizing a weighted average mechanism to assign a confidence score to the match between the first document and the second document; and
identifying one or more OCR errors in the first document, wherein identifying the one or more OCR errors include;
identifying missing information from the first document; and
determining a discrepancy in a correlation between a first term in the first document and a second term in the second document associated with same patient identifier as the first document, wherein the first term and the second term are different terms indicating a same concept;
correcting the one or more OCR errors by:
  supplementing the missing information in the first document from the second document, wherein the first document and the second document share same patient identifier; and
  associating the first term with the second term based on determination of a match percentage between the first term and the second term.

14. The computer system of claim 13, wherein the first document comprises a medical insurance document, and wherein the method further comprises transmitting an inquiry to the database to confirm a status of health insurance benefits associated with the medical insurance document prior to the patient attending an appointment.

15. The method of claim 14, wherein the method further comprises:
identifying the status of the health insurance benefits as being current;
reducing a payment for the appointment based on the current status of the health insurance benefits in real-time;
displaying a modified payment to the patient;
prompting the patient to pay the modified payment; and
in response to receiving the payment, processing the payment for the appointment.

16. The computer system of claim 13, wherein, in response to failing to verify the first document and the second document as being associated with the patient based on the comparison and predefined business rules, the method further comprises:
generating an alert; and
transmitting the alert to a human for reconciliation.

17. The computer system of claim 16, wherein the alert is selected from a group consisting of: an audio alert, a textual alert, and a graphical alert.

18. The method of claim 1, wherein the method further comprises:
determining if the match percentage between the first term of the first document and the second term of the second document is below a predetermined threshold; and
generating an alert based on the determination.

* * * * *